US00PP37442P3

(12) United States Plant Patent
Kievit

(10) Patent No.: US PP37,442 P3
(45) Date of Patent: May 26, 2026

(54) ***GERANIUM* PLANT NAMED 'Balgerpur103'**

(50) Latin Name: ***Geranium* interspecific**
Varietal Denomination: Balgerpur103

(71) Applicant: Ball Horticultural Company, West Chicago, IL (US)

(72) Inventor: Christa Kievit, Vessem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 19/356,152

(22) Filed: Oct. 12, 2025

(65) Prior Publication Data

US 2026/0114347 P1 Apr. 23, 2026

Related U.S. Application Data

(60) Provisional application No. 63/709,353, filed on Oct. 18, 2024.

(51) Int. Cl.
*A01H 5/02* (2018.01)
*A01H 6/42* (2018.01)

(52) U.S. Cl.
USPC ..... Plt./324
CPC ..... *A01H 6/42* (2018.05)

(58) Field of Classification Search
USPC ..... Plt./324
CPC ..... A01H 5/02
See application file for complete search history.

*Primary Examiner* — Kent L Bell
(74) *Attorney, Agent, or Firm* — Megan Bowman

(57) ABSTRACT

A new and distinct cultivar of *Geranium* plant named 'Balgerpur103', characterized by its dark purple-violet-colored flowers, dark, green-colored foliage, and vigorous, low-mounded growth habit, is disclosed.

1 Drawing Sheet

Latin name of genus and species of plant claimed: *Geranium* interspecific.

Variety denomination: 'Balgerpur103'.

BACKGROUND OF THE INVENTION

The present invention relates to a new and distinct cultivar of *Geranium* plant botanically known as *Geranium* interspecific and hereinafter referred to by the cultivar name 'Balgerpur103'.

The new cultivar originated in a controlled breeding program in Hem, the Netherlands during August 2018. The objective of the breeding program was the development of *Geranium* cultivars that flower uniformly and have large flowers, dark, green-colored foliage, and a vigorous, low-mounded growth habit.

The new *Geranium* cultivar is the result of cross-pollination. The female (seed) parent of the new cultivar is proprietary *Geranium sanguineum* breeding selection coded 2018-019, not patented, characterized by its single, pink-colored flowers, medium, green-colored foliage, and moderately vigorous, spreading growth habit. The male (pollen) parent of the new cultivar is *Geranium himalayense* 'Baby Blue', not patented, characterized by its single, lavender-blue colored flowers, medium, green-colored foliage, vigorous, semi-upright growth habit. The new cultivar was selected as a single flowering plant within the progeny of the above stated cross-pollination during August 2019 in a controlled environment in Hem, the Netherlands.

Asexual reproduction of the new cultivar by terminal stem cuttings since August 2019 in Hem, the Netherlands and West Chicago, Illinois, has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balgerpur103' as a new and distinct cultivar of *Geranium* plant:

1. Dark purple-violet colored flowers;
2. Dark, green-colored foliage; and
3. Vigorous, low-mounded growth habit.

Plants of the new cultivar differ from plants of the female parent primarily by having a mounded growth habit and longer flowering period. Plants of the new cultivar differ from plants of the male parent primarily by having a mounding habit and purple-violet-colored flowers.

Of the many commercially available *Geranium* cultivars, the most similar in comparison to the new cultivar is *Geranium* interspecific 'Rozanne', U.S. Plant Pat. No. 12,175. However, in side-by-side comparisons, plants of the new cultivar differ from plants of 'Rozanne' in at least the following characteristics:

1. Plants of the new cultivar have a flower color that has more purple coloration than flowers of plants of 'Rozanne'; and
2. Plants of the new cultivar flower earlier than plants of 'Rozanne'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'Balgerpur103'. The plants were approximately nine months old and grown in 3-quart containers for approximately six months in a double polyethylene greenhouse in Elburn, Illinois.

DETAILED BOTANICAL DESCRIPTION

Figure 1:
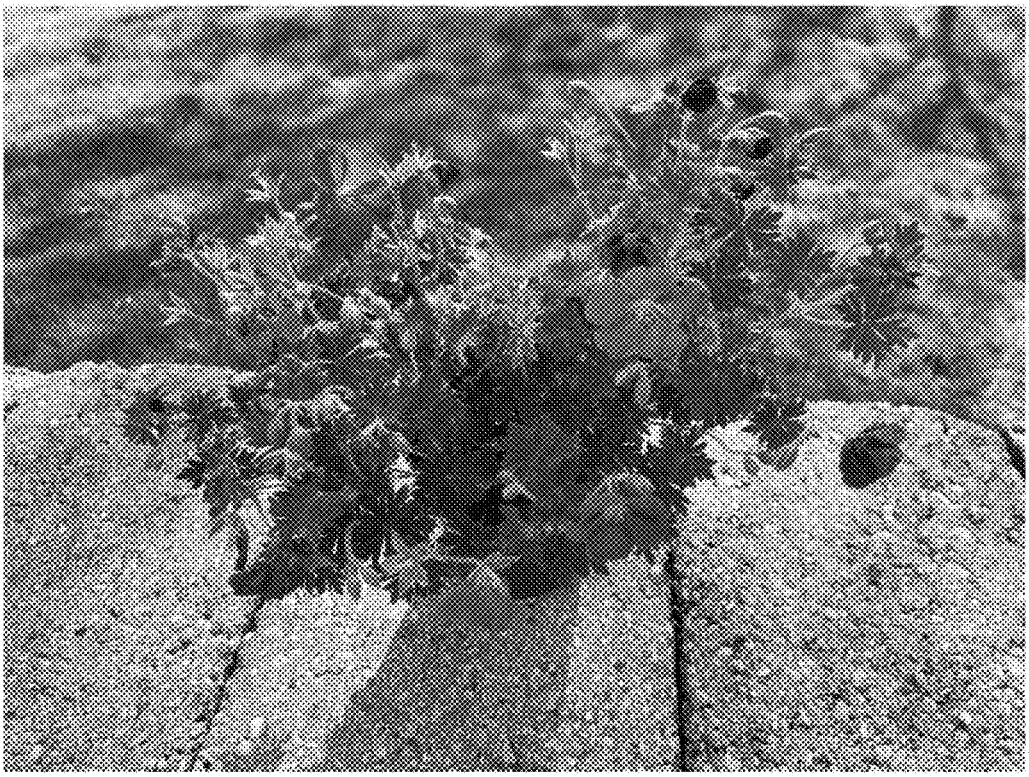
FIG. 1 illustrates a side view of the overall growth and flowering habit of 'Balgerpur103'.
Figure 2:
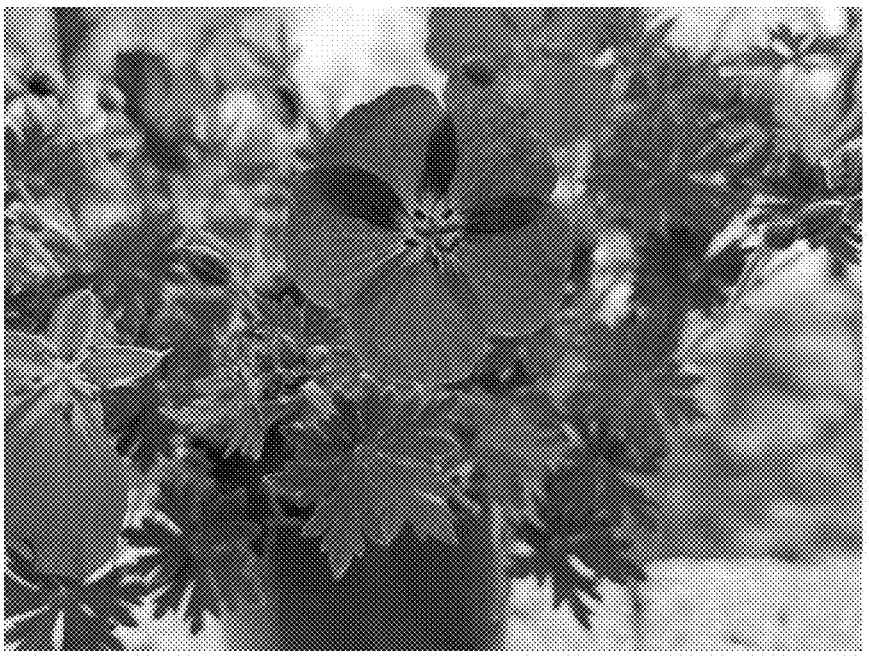
FIG. 2 illustrates a close-up view of an individual flower of 'Balgerpur103'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in April 2025 under natural light conditions in West Chicago, Illinois.

The following descriptions and measurements describe approximately nine-month-old plants produced from cuttings from stock plants and grown in a glass-covered greenhouse under conditions comparable to those used in commercial practice. The plants were grown in 3-quart containers for approximately six months in a double polyethylene greenhouse in Elburn, Illinois. Greenhouse temperatures were maintained at approximately 42° F. to 47° F. (5.6° C. to 8.3° C.) during the day and approximately 37° F. to 42° F. (2.8° C. to 5.0° C.) during the night. No supplemental lighting was used. Measurements and numerical values represent averages of typical plants.

Botanical classification: *Geranium* interspecific 'Balgerpur103'.

Parentage:

*Female parent*.—Proprietary *Geranium sanguineum* breeding selection coded 2018-019, not patented.

*Male parent*.—*Geranium himalayense* 'Baby Blue', not patented.

Propagation:

*Type cutting*.—Terminal stem.

*Time to initiate roots*.—Approximately 9 to 12 days.

*Time to produce a rooted cutting*.—Approximately 21 to 28 days.

*Root description*.—Fibrous.

*Rooting habit*.—Freely branching.

Plant description:

*Commercial crop time*.—Approximately 10 to 12 weeks from a rooted cutting to finish in a 15 cm pot.

*Growth habit and general appearance*.—Vigorous, low-mounded.

*Size*.—Height from soil level to top of plant: Approximately 13.0 cm. Width: Approximately 30.0 cm.

*Branching habit*.—Freely basal branching, pinching enhances basal branching. Quantity of main branches per plant: Approximately 6.

*Branch*.—Strength: Strong but flexible. Length: Approximately 12.0 cm. Diameter: Approximately 2.0 mm. Length of central internode: Approximately 4.0 cm. Texture: Densely pubescent. Color of young and mature stems: 144A.

Foliage description:

*General description*.—Quantity of leaves per branch: Approximately 8. Fragrance: Slight. Form: Simple, palmate, deeply-cleft with five to seven lobes. Arrangement: Opposite.

*Leaves*.—Aspect: Petiole is at an acute angle to stem; blade is perpendicular to stem. Shape: Reniform. Margin: Bicrenate, palmately lobed, somewhat wavy. Apex: Obtuse. Base: Cordate. Venation pattern: Palmate. Length of mature leaf: Approximately 3.0 cm. Width of mature leaf: Approximately 3.3 cm. Texture of upper and lower surfaces: Densely pubescent at the margins and venation. Color of upper surface of young and mature foliage: Closest to NN137A with venation of 146C. Color of lower surface of young and mature foliage: Closest to 137B with venation of 146C.

*Petiole*.—Length: Approximately 1.5 to 3.5 cm. Diameter: Approximately 1.0 mm. Texture: Densely pubescent. Color: 144B.

*Stipule*.—Four per node, lanceolate. Length: Approximately 3.0 to 4.0 mm. Width: 2.0 mm. Color: Nearest 138D with an overlay of 144B. Texture: Densely pubescent.

Flowering description:

*Flowering habit*.—'Balgerpur103' is freely flowering under outdoor growing conditions with substantially continuous blooming from early spring to late spring.

*Lastingness of individual flower on the plant*.—Approximately 3 to 7 days.

Inflorescence description:

*General description*.—Type: Dichasial cyme with two to five flowers per cyme. Fragrance: Slight. Length or height: Approximately 4.0 cm. Width: Approximately 5.0 cm. Quantity of fully open flowers per inflorescence: Approximately 10.

*Peduncle*.—Strength: Strong. Aspect: Erect. Length: Approximately 7.5 cm. Diameter: Approximately 1.0 mm. Texture: Densely pubescent with a mixture of glandular and nonglandular hairs. Gland color: Colorless, transparent. Color: 144B.

Flower description:

*General description*.—Type: Single, actinomorphic.

*Bud*.—Rate of opening: Generally, takes 3 to 7 days for bud to progress from first color to fully open flower.

*Bud just before opening*.—Shape: Elliptic. Length: Approximately 1.0 cm. Width: Approximately 8.0 mm. Sepal texture: Densely pubescent with a mixture of glandular and nonglandular hairs. Gland color: Colorless, transparent. Petal texture: Glabrous. Petal color: N82A.

*Corolla*.—Shape: Rotate. Diameter: Approximately 3.0 cm. Depth: Approximately 1.0 cm.

*Petals*.—Quantity: Five petals. Shape: Obovate. Appearance: Matte. Margin: Entire. Apex: Obtuse to slightly notched. Base: Attenuate. Length of petals: Approximately 1.7 cm. Width of petals: Approximately 1.5 cm. Texture of upper and lower surfaces: Glabrous. Color of upper surface of petals when fully open: N88A with venation of 77B and NN155C at the base. Color of lower surface of petals when fully open: N88B with venation of 77D and N155C at the base.

*Calyx*.—Shape: 5-pointed star. Diameter: Approximately 1.7 cm.

*Sepals*.—Quantity per flower: Approximately 5, fused at base. Shape: Lanceolate. Margin: Entire. Apex: Acuminate. Length: Approximately 1.0 cm. Width: Approximately 3.0 mm. Texture of inner surface: Glabrous. Texture of outer surface: Densely pubescent with a mixture of glandular and nonglandular hairs. Gland color: Colorless, transparent. Color of upper and lower surface: 143A to 143D near the base. Color of lower surface: 138A with an overlay of 138D at base.

*Pedicel*.—Strength: Strong, flexible. Aspect: Acute angle to peduncle. Length: Approximately 1.5 cm. Diameter: Approximately 1.0 mm. Texture: Densely pubescent with a mixture of glandular and nonglandular hairs. Gland color: Colorless, transparent. Color: 144B.

*Reproductive organs*.—Androecium: Quantity of mature stamens: Approximately 10 per flower. Anther shape: Oblong. Anther length: Approximately 1.5 mm. Anther color: Closest to N89A. Filament length: Approximately 8.0 mm. Filament color: NN155D tinted with N89A nearest anther. Pollen amount: Moderate. Pollen color: 90D. Gynoecium: Pistil quantity: 1 per flower. Pistil length: Approximately 1.0 cm. Stigma shape: 5 branched. Stigma length: Approximately 2.0 mm. Stigma color: 58A. Style length: Approximately 3.0 mm. Style color: Closest to 58A. Ovary length: Approximately 2.0 mm. Ovary texture: Glabrous. Ovary color: 145A.

Seed and fruit production: Neither seed nor fruit production has been observed.

Disease and pest resistance: Resistance to pathogens and pests common to *Geranium* has not been observed.

What is claimed is:

1. A new and distinct cultivar of *Geranium* plant named 'Balgerpur103', substantially as herein illustrated and described.

* * * * *